United States Patent
Cormier et al.

(10) Patent No.: US 8,663,155 B2
(45) Date of Patent: Mar. 4, 2014

(54) TRANSDERMAL DRUG DELIVERY DEVICES HAVING COATED MICROPROTRUSIONS

(75) Inventors: Michel J. N. Cormier, Mountain View, CA (US); Wendy A. Young, San Jose, CA (US); Kofi Nyam, Palo Alto, CA (US); Peter E. Daddona, Menlo Park, CA (US); Wei-Qi Lin, Palo Alto, CA (US)

(73) Assignee: Alza Corporation, Vacaville, CA (US)

( * ) Notice: Subject to any disclaimer, the term of this patent is extended or adjusted under 35 U.S.C. 154(b) by 606 days.

(21) Appl. No.: 11/347,779

(22) Filed: Feb. 2, 2006

(65) Prior Publication Data

US 2006/0200069 A1    Sep. 7, 2006

Related U.S. Application Data

(63) Continuation of application No. 10/045,842, filed on Oct. 26, 2001.

(60) Provisional application No. 60/244,038, filed on Oct. 26, 2000.

(51) Int. Cl.
*A61M 37/00* (2006.01)

(52) U.S. Cl.
CPC .................................. *A61M 37/0015* (2013.01)
USPC .......................................................... 604/46

(58) Field of Classification Search
None
See application file for complete search history.

(56) References Cited

U.S. PATENT DOCUMENTS

| | | |
|---|---|---|
| 3,136,314 A | 6/1964 | Kravitz |
| RE25,637 E | 9/1964 | Kravitz et al. |
| 3,470,011 A | 9/1969 | Szumski et al. |
| 3,814,097 A | 6/1974 | Ganderton et al. |
| 3,964,482 A | 6/1976 | Gerstel et al. |
| 4,109,655 A | 8/1978 | Chacornac |
| 4,453,926 A | 6/1984 | Galy |
| 5,250,023 A | 10/1993 | Lee et al. |
| 5,279,544 A | 1/1994 | Gross et al. |
| 5,298,256 A | 3/1994 | Flockhart et al. |
| 5,321,008 A | 6/1994 | Beaumont et al. |
| 5,457,041 A * | 10/1995 | Ginaven et al. ............. 435/455 |
| 5,487,726 A | 1/1996 | Reabenau et al. |
| 5,738,728 A | 4/1998 | Tisone |
| 5,741,554 A | 4/1998 | Tisone |
| 5,743,960 A | 4/1998 | Tisone |
| 5,879,326 A | 3/1999 | Godshall et al. |
| 5,916,524 A | 6/1999 | Tisone |
| 5,985,316 A * | 11/1999 | Gyory et al. ................. 424/449 |

(Continued)

FOREIGN PATENT DOCUMENTS

| | | |
|---|---|---|
| CH | 580961 | 10/1976 |
| EP | 0 278 474 | 2/1988 |

(Continued)

*Primary Examiner* — Brian Gulledge

(74) *Attorney, Agent, or Firm* — Sunstein Kann Murphy & Timbers LLP

(57) ABSTRACT

A device (12) and method are provided for percutaneous transdermal delivery of a potent pharmacologically active agent. The agent is dissolved in water to form an aqueous coating solution having an appropriate viscosity for coating extremely tiny skin piercing elements (10). The coating solution is applied to the skin piercing elements (10) using known coating techniques and then dried. The device (12) is applied to the skin of a living animal (e.g., a human), causing the microprotrusions (10) to pierce the stratum corneum and deliver a therapeutically effect dose of the agent to the animal.

17 Claims, 5 Drawing Sheets

(56) References Cited

U.S. PATENT DOCUMENTS

| | | |
|---|---|---|
| 6,050,988 A | 4/2000 | Zuck |
| 6,083,196 A | 7/2000 | Trautman et al. |
| 6,091,975 A | 7/2000 | Daddona et al. |
| 6,230,051 B1 | 5/2001 | Cormier et al. |
| 6,322,808 B1 * | 11/2001 | Trautman et al. ............ 424/448 |
| 6,537,242 B1 | 3/2003 | Palmer |
| 6,589,202 B1 | 7/2003 | Powell |
| 6,855,131 B2 | 2/2005 | Trautman et al. |
| 6,855,372 B2 | 2/2005 | Trautman et al. |
| 6,918,901 B1 | 7/2005 | Theeuwes et al. |
| 6,953,589 B1 | 10/2005 | Trautman et al. |
| 7,097,631 B2 | 8/2006 | Trautman et al. |
| 7,131,960 B2 | 11/2006 | Trautman et al. |
| 7,184,826 B2 | 2/2007 | Cormier et al. |
| 2002/0087182 A1 | 7/2002 | Trautman et al. |
| 2002/0102292 A1 | 8/2002 | Cormier et al. |
| 2002/0132054 A1 * | 9/2002 | Trautman et al. ......... 427/372.2 |
| 2002/0177839 A1 | 11/2002 | Cormier et al. |
| 2003/0181936 A1 | 9/2003 | Trautman et al. |
| 2003/0199810 A1 | 10/2003 | Trautman et al. |
| 2004/0062813 A1 | 4/2004 | Cormier et al. |
| 2004/0138610 A1 | 7/2004 | Cormier et al. |
| 2004/0236271 A1 | 11/2004 | Theeuwes et al. |
| 2004/0265354 A1 | 12/2004 | Ameri et al. |
| 2005/0084604 A1 | 4/2005 | Trautman et al. |
| 2005/0106209 A1 | 5/2005 | Ameri et al. |
| 2005/0106227 A1 | 5/2005 | Zalipsky et al. |
| 2005/0123507 A1 | 6/2005 | Ameri et al. |
| 2005/0148926 A1 | 7/2005 | Trautman et al. |
| 2005/0234401 A1 | 10/2005 | Trautman et al. |
| 2005/0256045 A1 | 11/2005 | Ameri |
| 2006/0095061 A1 | 5/2006 | Trautman et al. |
| 2006/0142691 A1 | 6/2006 | Cormier et al. |
| 2006/0177494 A1 | 8/2006 | Cormier et al. |
| 2006/0188555 A1 | 8/2006 | Cormier et al. |

FOREIGN PATENT DOCUMENTS

| | | | |
|---|---|---|---|
| EP | 0 407 063 | | 6/1990 |
| JP | 2000-185106 | | 7/2000 |
| WO | WO 93/17754 | | 9/1993 |
| WO | WO 96/10630 | | 4/1996 |
| WO | WO 96/17648 | | 7/1996 |
| WO | WO 96/37155 | | 11/1996 |
| WO | WO 96/37256 | | 11/1996 |
| WO | WO 97/03718 | | 2/1997 |
| WO | WO97/47254 | | 12/1997 |
| WO | WO 97/48440 | | 12/1997 |
| WO | WO 97/48441 | | 12/1997 |
| WO | WO 97/48442 | | 12/1997 |
| WO | WO 98/00193 | | 1/1998 |
| WO | WO 98/11937 | | 3/1998 |
| WO | WO 98/20861 | | 5/1998 |
| WO | WO 98/28037 | | 7/1998 |
| WO | WO 98/29298 | | 7/1998 |
| WO | WO 98/29365 | | 7/1998 |
| WO | WO 99/64580 | | 12/1999 |
| WO | WO 00/44438 | * | 8/2000 ............... A61N 1/30 |
| WO | WO 02/07813 | | 1/2002 |

\* cited by examiner

TRANSDERMAL DRUG DELIVERY DEVICES HAVING COATED MICROPROTRUSIONS

CROSS REFERENCE TO RELATED APPLICATIONS

This application is a continuation of application Ser. No. 10/045,842, filed Oct. 26, 2001, pending, which claims the benefit of U.S. Provisional Application No. 60/244,038, filed Oct. 26, 2000. These documents are incorporated by reference herein in their entirety.

TECHNICAL FIELD

This invention relates to administering and enhancing transdermal delivery of an agent across the skin. More particularly, the invention relates to a percutaneous drug delivery system for administering a potent pharmacologically active agent through the stratum corneum using skin piercing microprotrusions which have a dry coating of the pharmacologically active agent. Delivery of the agent is facilitated when the microprotrusions pierce the skin of a patient and the patient's interstitial fluid contacts and dissolves the active agent.

BACKGROUND ART

Drugs are most conventionally administered either orally or by injection. Unfortunately, many medicaments are completely ineffective or have radically reduced efficacy when orally administered since they either are not absorbed or are adversely affected before entering the bloodstream and thus do not possess the desired activity. On the other hand, the direct injection of the medicament into the bloodstream, while assuring no modification of the medicament during administration, is a difficult, inconvenient, painful and uncomfortable procedure, sometimes resulting in poor patient compliance.

Hence, in principle, transdermal delivery provides for a method of administering drugs that would otherwise need to be delivered via hypodermic injection or intravenous infusion. Transdermal drug delivery offers improvements in both of these areas. Transdermal delivery when compared to oral delivery avoids the harsh environment of the digestive tract, bypasses gastrointestinal drug metabolism, reduces first-pass effects, and avoids the possible deactivation by digestive and liver enzymes. Conversely, the digestive tract is not subjected to the drug during transdermal administration. Indeed, many drugs such as aspirin have an adverse effect on the digestive tract. However, in many instances, the rate of delivery or flux of many agents via the passive transdermal route is too limited to be therapeutically effective.

The word "transdermal" is used herein as a generic term referring to passage of an agent across the skin layers. The word "transdermal" refers to delivery of an agent (e.g., a therapeutic agent such as a drug) through the skin to the local tissue or systemic circulatory system without substantial cutting or piercing of the skin, such as cutting with a surgical knife or piercing the skin with a hypodermic needle. Transdermal agent delivery includes delivery via passive diffusion as well as by external energy sources including electricity (e.g., iontophoresis) and ultrasound (e.g., phonophoresis). While drugs do diffuse across both the stratum corneum and the epidermis, the rate of diffusion through the stratum corneum is often the limiting step. Many compounds, in order to achieve a therapeutic dose, require higher delivery rates than can be achieved by simple passive transdermal diffusion. When compared to injections, transdermal agent delivery eliminates the associated pain and reduces the possibility of infection.

Theoretically, the transdermal route of agent administration could be advantageous in the delivery of many therapeutic proteins, because proteins are susceptible to gastrointestinal degradation and exhibit poor gastrointestinal uptake and transdermal devices are more acceptable to patients than injections. However, the transdermal flux of medically useful peptides and proteins is often insufficient to be therapeutically effective due to the large size/molecular weight of these molecules. Often the delivery rate or flux is insufficient to produce the desired effect or the agent is degraded prior to reaching the target site, for example while in the patient's bloodstream.

Transdermal drug delivery systems generally rely on passive diffusion to administer the drug while active transdermal drug delivery systems rely on an external energy source (e.g., electricity) to deliver the drug. Passive transdermal drug delivery systems are more common. Passive transdermal systems have a drug reservoir containing a high concentration of drug adapted to contact the skin where the drug diffuses through the skin and into the body tissues or bloodstream of a patient. The transdermal drug flux is dependent upon the condition of the skin, the size and physical/chemical properties of the drug molecule, and the concentration gradient across the skin. Because of the low permeability of the skin to many drugs, transdermal delivery has had limited applications. This low permeability is attributed primarily to the stratum corneum, the outermost skin layer which consists of flat, dead cells filled with keratin fibers (keratinocytes) surrounded by lipid bilayers. This highly-ordered structure of the lipid bilayers confers a relatively impermeable character to the stratum corneum.

One common method of increasing the passive transdermal diffusional drug flux involves pre-treating the skin with, or co-delivering with the drug, a skin permeation enhancer. A permeation enhancer, when applied to a body surface through which the drug is delivered, enhances the flux of the drug therethrough. However, the efficacy of these methods in enhancing transdermal protein flux has been limited, at least for the larger proteins, due to their size.

Active transport systems use an external energy source to assist drug flux through the stratum corneum. One such enhancement for transdermal drug delivery is referred to as "electrotransport." This mechanism uses an electrical potential, which results in the application of electric current to aid in the transport of the agent through a body surface, such as skin. Other active transport systems use ultrasound (phonophoresis) and heat as the external energy source.

There also have been many attempts to mechanically penetrate or disrupt the outermost skin layers thereby creating pathways into the skin in order to enhance the amount of agent being transdermally delivered. Early vaccination devices known as scarifiers generally had a plurality of tines or needles which are applied to the skin to and scratch or make small cuts in the area of application. The vaccine was applied either topically on the skin, such as U.S. Pat. No. 5,487,726 issued to Rabenau or as a wetted liquid applied to the scarifier tines such as U.S. Pat. No. 4,453,926 issued to Galy, or U.S. Pat. No. 4,109,655 issued to Chacornac, or U.S. Pat. No. 3,136,314 issued to Kravitz. Scarifiers have been suggested for intradermal vaccine delivery in part because only very small amounts of the vaccine need to be delivered into the skin to be effective in immunizing the patient. Further, the amount of vaccine delivered is not particularly critical since an excess amount achieves satisfactory immunization as well as a minimum amount. However a serious disadvantage in using a scarifier to deliver a drug is the difficulty in determining the transdermal drug flux and the resulting dosage delivered. Also due to the elastic, deforming and resilient nature of skin to deflect and resist puncturing, the tiny piercing elements often do not uniformly penetrate the skin and/or are wiped free of a liquid coating of an agent upon skin penetration. Additionally, due to the self healing process of the skin, the punctures or slits made in the skin tended to close up after removal of the piercing elements from the stratum corneum. Thus, the elastic nature of the skin acts to remove the active agent coating which has been applied to the tiny piercing elements upon penetration of these elements into the skin. Furthermore the tiny slits formed by the piercing elements heal quickly after removal of the device, thus limiting the passage of agent through the passageways created by the piercing elements and in turn limiting the transdermal flux of such devices.

Other devices which use tiny skin piercing elements to enhance transdermal drug delivery are disclosed in European Patent EP 0407063A1, U.S. Pat. No. 5,879,326 issued to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365; all incorporated by reference in their entirety. These devices use piercing elements of various shapes and sizes to pierce the outermost layer (i.e., the stratum corneum) of the skin. The piercing elements disclosed in these references generally extend perpendicularly from a thin, flat member, such as a pad or sheet. The piercing elements in some of these devices are extremely small, some having dimensions (i.e., a microblade length and width) of only about 25-400 µm and a microblade thickness of only about 5-50 µm. These tiny piercing/cutting elements make correspondingly small microslits/microcuts in the stratum corneum for enhanced transdermal agent delivery therethrough.

Generally, these systems include a reservoir for holding the drug and also a delivery system to transfer the drug from the reservoir through the stratum corneum, such as by hollow tines of the device itself. One example of such a device is disclosed in WO 93/17754 which has a liquid drug reservoir. The reservoir must be pressurized to force the liquid drug through the tiny tubular elements and into the skin. Disadvantages of devices such as these include the added complication and expense for adding a pressurizable liquid reservoir and complications due to the presence of a pressure-driven delivery system.

DISCLOSURE OF THE INVENTION

The device and method of the present invention overcome these limitations by transdermally delivering a pharmacologically active agent using a microprotrusion device having microprotrusions which are coated with a dry coating containing the agent. The present invention is directed to a device and method for delivering a pharmacologically active agent through the stratum corneum of preferably a mammal and most preferably a human, by coating a plurality of stratum corneum-piercing microprotrusions with a high potency pharmacologically active agent. The agent is selected to be sufficiently potent to be therapeutically effective when delivered as a dry coating on a plurality of skin piercing microprotrusions. Further, the agent must have sufficient water solubility to form an aqueous coating solution having the necessary solubility and viscosity for coating the microprotrusions.

A preferred embodiment of this invention consists of a device for delivering a beneficial agent through the stratum corneum. The device comprises a member having a plurality, and preferably a multiplicity, of stratum corneum-piercing microprotrusions. Each of the microprotrusions has a length of less than 500 µm, or if longer than 500 µm, then means are provided to ensure that the microprotrusions penetrate the skin to a depth of no more than 500 µm. These microprotrusions have a dry coating thereon. The coating, before drying, comprises an aqueous solution of a high potency pharmacologically active agent. The pharmacologically active agent is sufficiently potent to be pharmaceutically effective in a dose of less than about 1 mg and preferably less than about 0.25 mg, per application. The pharmacologically active agent is selected to have a water solubility of greater than about 50 mg/ml and the composition has a viscosity less than about 500 centipoises (cp) in order to effectively coat the microprotrusions. The solution, once coated onto the surfaces of the microprotrusions, provides a pharmaceutically effective amount of the pharmacologically active agent. The coating is further dried onto the microprotrusions using drying methods known in the art.

Another preferred embodiment of this invention consists of a method of making a device for transdermally delivering a pharmacologically active agent. The method comprises providing a member having a plurality of stratum corneum-piercing microprotrusions. An aqueous solution of the pharmacologically active agent is applied to the microprotrusions and then dried to form a dry agent-containing coating thereon. The pharmacologically active agent is sufficiently potent to be pharmaceutically effective in a dose of less than about 1 mg, and preferably less than about 0.25 mg, per application. The pharmacologically active agent must have a water solubility of greater than about 50 mg/ml, preferably greater than about 100 mg/ml, and the coating solution must have a viscosity at 25° C. of less than about 500 cp preferably less than about 50 cp, in order to effectively coat the microprotrusions. The composition can be prepared at any temperature as long as the pharmacologically active agent is not rendered inactive due to the conditions. The solution, once coated onto the surfaces of the microprotrusions, provides a pharmaceutically effective amount of the pharmacologically active agent.

The coating thickness is preferably less than the thickness of the microprotrusions, more preferably the thickness is less than 50 µm and most preferably less than 25 µm. Generally, the coating thickness is an average thickness measured over the microprotrusions.

The pharmacologically active agent for coating the microprotrusions is selected to have sufficient potency to be therapeutically effective when administered transdermally in an amount of less than about 1 mg, and preferably less than about 0.25 mg, of active agent.

The most preferred agents are selected from the group consisting of ACTH (1-24), calcitonin, desmopressin, LHRH, LHRH analogs, goserelin, leuprolide, PTH, vasopressin, deamino [Val4, D-Arg8] arginine vasopressin, buserelin, triptorelin, interferon alpha, interferon beta, interferon gamma, FSH, EPO, GM-CSF, G-CSF, IL-10, glucagon, growth hormone releasing factor (GRF) and analogs of these agents including pharmaceutically acceptable salts thereof.

The coating can be applied to the microprotrusions using known coating methods. For example, the microprotrusions can be immersed into an aqueous coating solution of the agent. Alternatively the coating solution can be sprayed onto the microprotrusions. Preferably the spray has a droplet size of about 10-200 picoliters. More preferably the droplet size and placement is precisely controlled using printing techniques so that the coating solution is deposited directly onto the microprotrusions and not onto other "non-piercing" portions of the member having the microprotrusions.

In another aspect of the invention, the stratum corneum-piercing microprotrusions are formed from a sheet wherein the microprotrusions are formed by etching or punching the sheet and then the microprotrusions are folded or bent out of a plane of the sheet. While the pharmacologically active agent coating can be applied to the sheet before formation of the microprotrusions, preferably the coating is applied after the microprotrusions are cut or etched out but prior to being folded out of the plane of the sheet. More preferred is coating after the microprotrusions have been folded or bent from the plane of the sheet.

BRIEF DESCRIPTION OF THE DRAWINGS

The invention will now be described in greater detail with reference to the preferred embodiments illustrated in the accompanying drawings and figures. wherein.

MODES FOR CARRYING OUT THE INVENTION

Definitions

Figure 1:
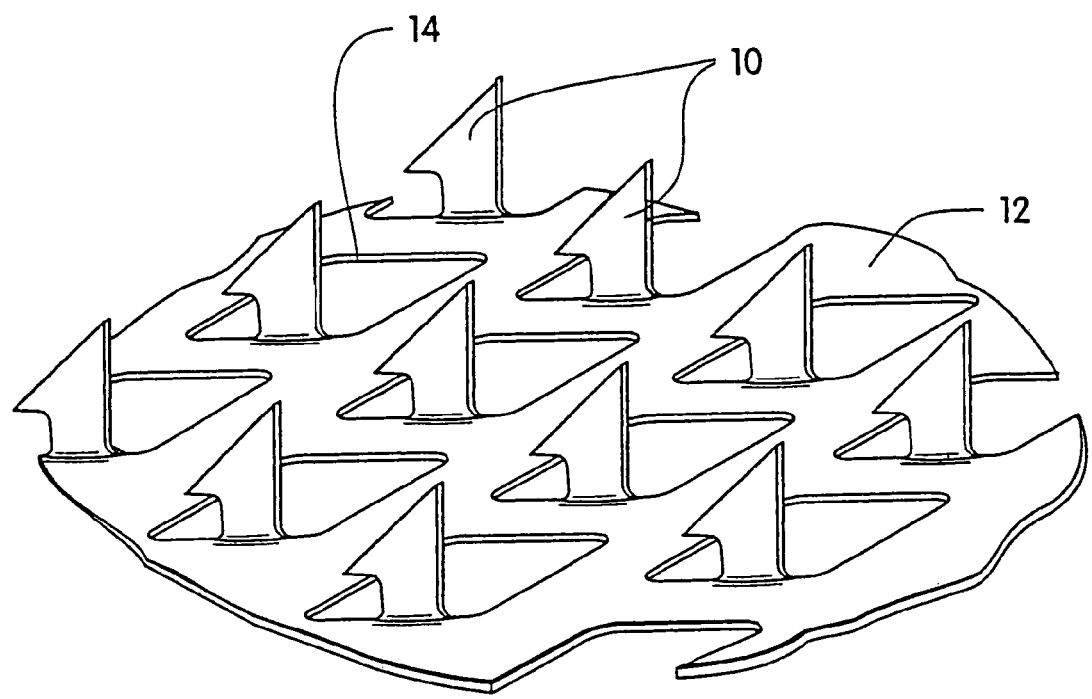
FIG. 1 is a perspective view of a portion of one example of a microprotrusion array.

Unless stated otherwise the following terms used herein have the following meanings.

The term "transdermal" means the delivery of an agent into and/or through the skin for local or systemic therapy.

The term "transdermal flux" means the rate of transdermal delivery.

The term "co-delivering" as used herein means that a supplemental agent(s) is administered transdermally either before the agent is delivered, before and during transdermal flux of the agent, during transdermal flux of the agent, during and after transdermal flux of the agent, and/or after transdermal flux of the agent.

Additionally, two or more agents may be coated onto the microprotrusions resulting in co-delivery of the agents.

The term "pharmacologically active agent" as used herein refers to a non-immunogenic drug or a composition of matter or mixture containing a non-immunogenic drug which is pharmacologically effective when administered in an amount of less than about 1 mg, and preferably less than about 0.25 mg. Thus, the term "pharmacologically active agent" encompasses only very potent drugs that are pharmacologically effective at very low doses and specifically excludes vaccines. Examples of such high potency pharmacologically active agents include, without limitation, leutinizing hormone releasing hormone (LHRH), LHRH analogs (such as goserelin, leuprolide, buserelin, triptorelin, gonadorelin, and napfarelin, menotropins (urofollitropin (follicle stimulating hormone (FSH) and LH)), vasopressin, desmopressin, adrenocortiocotropic hormone (ACTH), ACTH analogs such as ACTH (1-24), calcitonin, parathyroid hormone (PTH), vasopressin, deamino [Val4, D-Arg8] arginine vasopressin, interferon alpha, interferon beta, interferon gamma, erythropoietin (EPO), granulocyte macrophage colony stimulating factor (GM-CSF), granulocyte colony stimulating factor (G-CSF), interleukin-10 (IL-10) and glucagon. It is to be understood that more than one agent may be incorporated into the agent formulation in the method of this invention, and that the use of the term "pharmacologically active agent" in no way excludes the use of two or more such agents or drugs. The agents can be in various forms, such as free bases, acids, charged or uncharged molecules, components of molecular complexes or nonirritating, pharmacologically acceptable salts. Also, simple derivatives of the agents (such as ethers, esters, amides, etc) which are easily hydrolyzed at body pH, enzymes, etc., can be employed.

The term "therapeutically effective amount" or "therapeutically effective rate" refers to the amount or rate of the pharmacologically active agent needed to effect the desired therapeutic, often beneficial, result. The amount of agent employed in the coatings will be that amount necessary to deliver a therapeutically effective amount of the agent to achieve the desired therapeutic result. In practice, this will vary widely depending upon the particular pharmacologically active agent being delivered, the site of delivery, the severity of the condition being treated, the desired therapeutic effect and the dissolution and release kinetics for delivery of the agent from the coating into skin tissues. It is not practical to define a precise range for the therapeutically effective amount of the pharmacologically active agent incorporated into the microprotrusions and delivered transdermally according to the methods described herein. However, generally such agents utilized in the device of the present invention are defined as potent pharmacologically active agents since the microprotrusions are sized with a limited surface area for carrying the coating. In general, the amount of the agent needed to achieve the desired therapy is less than about 1 mg, more preferably less than 0.25 mg.

The term "microprotrusions" refers to piercing elements which are adapted to pierce or cut through the stratum corneum into the underlaying epidermis layer, or epidermis and dermis layers, of the skin of a living animal, particularly a human. The piercing elements should not pierce the skin to a depth which causes bleeding. Typically the piercing elements have a blade length of less than 500 µm, and preferably less than 250 µm. The microprotrusions typically have a width and thickness of about 5 to 50 µm. The microprotrusions may be formed in different shapes, such as needles, hollow needles, blades, pins, punches, and combinations thereof.

The term "microprotrusion array" as used herein refers to a plurality of microprotrusions arranged in an array for piercing the stratum corneum. The microprotrusion array may be formed by etching or punching a plurality of microprotrusions from a thin sheet and folding or bending the microprotrusions out of the plane of the sheet to form a configuration such as that shown in FIG. 1. The microprotrusion array may also be formed in other known manners, such as by forming one or more strips having microprotrusions along an edge of each of the strip(s) as disclosed in Zuck, U.S. Pat. No. 6,050,988. The microprotrusion array may include hollow needles which hold a dry pharmacologically active agent.

References to the area of the sheet or member and reference to some property per area of the sheet or member, are referring to the area bounded by the outer circumference or border of the sheet.

The term "pattern coating" refers to coating an agent onto selected areas of the microprotrusions. More than one agent may be pattern coated onto a single microprotrusion array. Pattern coatings can be applied to the microprotrusions using known micro-fluid dispensing techniques such as micropipeting and ink jet coating.

DETAILED DESCRIPTION

The present invention provides a device for transdermally delivering a pharmacologically active agent to a patient in need thereof. The device has a plurality of stratum corneum-piercing microprotrusions extending therefrom. The microprotrusions are adapted to pierce through the stratum corneum into the underlying epidermis layer, or epidermis and dermis layers, but do not penetrate so deep as to reach the capillary beds and cause significant bleeding. The microprotrusions have a dry coating thereon which contains the pharmacologically active agent. Upon piercing the stratum corneum layer of the skin, the agent-containing coating is dissolved by body fluid (intracellular fluids and extracellular fluids such as interstitial fluid) and released into the skin for local or systemic therapy.

The kinetics of the agent-containing coating dissolution and release will depend on many factors including the nature of the drug, the coating process, the coating thickness and the coating composition (e.g., the presence of coating formulation additives). Depending on the release kinetics profile, it may be necessary to maintain the coated microprotrusions in piercing relation with the skin for extended periods of time (e.g., up to about 8 hours). This can be accomplished by anchoring the microprotrusion member to the skin using adhesives or by using anchored microprotrusions such as described in WO 97/48440, incorporated by reference in its entirety.

FIG. 1 illustrates one embodiment of a stratum corneum-piercing microprotrusion member for use with the present invention. FIG. 1 shows a portion of the member having a plurality of microprotrusions 10. The microprotrusions 10 extend at substantially a 90° angle from a sheet 12 having openings 14. The sheet 12 may be incorporated in a delivery patch including a backing for the sheet 12 and may additionally include adhesive for adhering the patch to the skin. In this embodiment the microprotrusions are formed by etching or punching a plurality of microprotrusions 10 from a thin metal sheet 12 and bending the microprotrusions 10 out of a plane of the sheet. Metals such as stainless steel and titanium are preferred. Metal microprotrusion members are disclosed in Trautman et al, U.S. Pat. No. 6,083,196; Zuck U.S. Pat. No. 6,050,988; and Daddona et al., U.S. Pat. No. 6,091,975; the disclosures of which are incorporated herein by reference. Other microprotrusion members that can be used with the present invention are formed by etching silicon using silicon chip etching techniques or by molding plastic using etched micro-molds. Silicon and plastic microprotrusion members are disclosed in Godshall et al., U.S. Pat. No. 5,879,326, the disclosures of which are incorporated herein by reference.

Figure 2:
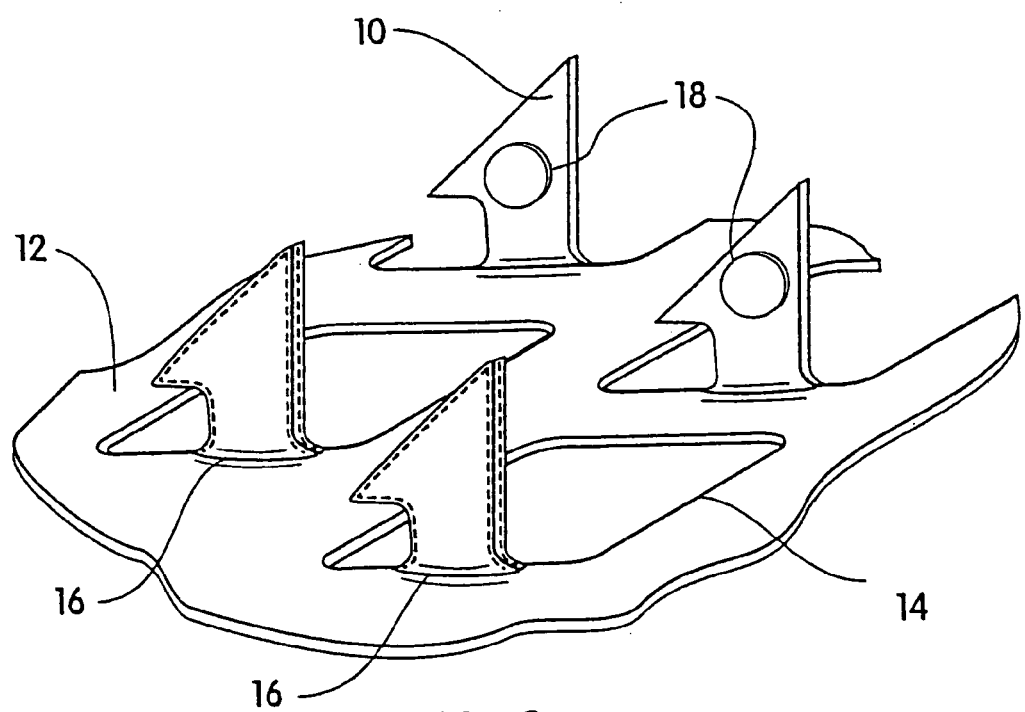
FIG. 2 is a perspective view of the microprotrusion array of FIG. 1 with a coating deposited onto the microprotrusions.

FIG. 2 illustrates the microprotrusion member having microprotrusions 10 having a pharmacologically active agent-containing coating 16. The coating 16 may partially or completely cover the microprotrusion 10. For example, the coating can be in a dry pattern coating on the microprotrusions. The coatings can be applied before or after the microprotrusions are formed.

The coating on the microprotrusions can be formed by a variety of known methods. One such method is dip-coating. Dip-coating can be described as a means to coat the microprotrusions by partially or totally immersing the microprotrusions into the drug-containing coating solution. Alternatively the entire device can be immersed into the coating solution. Coating only those portions the microprotrusion member which pierce the skin is preferred.

By use of the partial immersion technique described above, it is possible to limit the coating to only the tips of the microprotrusions. There is also a roller coating mechanism that limits the coating to the tips of the microprotrusion. This technique is described in a U.S. provisional patent (Ser. No. 60/276,762) filed 16 Mar. 2001, which is fully incorporated herein by reference.

Other coating methods include spraying the coating solution onto the microprotrusions. Spraying can encompass formation of an aerosol suspension of the coating composition. In a preferred embodiment an aerosol suspension forming a droplet size of about 10 to 200 picoliters is sprayed onto the microprotrusions and then dried. In another embodiment, a very small quantity of the coating solution can be deposited onto the microprotrusions as a pattern coating 18. The pattern coating 18 can be applied using a dispensing system for positioning the deposited liquid onto the microprotrusion surface. The quantity of the deposited liquid is preferably in the range of 0.5 to 20 nanoliters/microprotrusion. Examples of suitable precision metered liquid dispensers are disclosed in U.S. Pat. Nos. 5,916,524; 5,743,960; 5,741,554; and 5,738,728 the disclosures of which are incorporated herein by reference. Microprotrusion coating solutions can also be applied using ink jet technology using known solenoid valve dispensers, optional fluid motive means and positioning means which is generally controlled by use of an electric field. Other liquid dispensing technology from the printing industry or similar liquid dispensing technology known in the art can be used for applying the pattern coating of this invention.

The coating solutions used in the present invention are aqueous solutions of the pharmacologically active agent. The solution must have a viscosity of less than about 500 cp, and preferably less than about 50 cp, in order to effectively coat the tiny stratum corneum-piercing elements to an appropriate thickness. As mentioned above, the pharmacologically active agent must have an aqueous solubility greater than about 50 mg/ml and preferably greater than about 100 mg/ml in the coating solution.

Desired coating thickness is dependent upon the density of the microprotrusions per unit area of the sheet and the viscosity and concentration of the coating composition as well as the coating method chosen. In general, coating thickness must be less than 50 micrometers since thicker coatings have a tendency to slough off the microprotrusions upon stratum corneum piercing. A preferred coating thickness is less than 10 micrometers as measured from the microprotrusion surface. Generally coating thickness is referred to as an average coating thickness measured over the coated microprotrusion. A more preferred coating thickness is about 1 to 10 micrometers.

The agents used in the present invention are high potency agents requiring a dose of about 1 mg or less, preferably about 0.25 mg or less. Amounts within this range can be coated onto a microprotrusion array of the type shown in FIG. 1 having the sheet 12 with an area of up to 10 $cm^2$ and a microprotrusion density of up to 500 microprotrusions per $cm^2$.

Preferred pharmacologically active agents having the properties described above are selected from the group consisting of desmopressin, luteinizing hormone releasing hormone (LHRH) and LHRH analogs (e.g., goserelin, leuprolide, buserelin, triptorelin), parathyroid hormone (PTH), calcitonin, vasopressin, deamino [Val4, D-Arg8] arginine vasopressin, interferon alpha, interferon beta, interferon gamma, menotropins (urofollotropin (follicle stimulating hormone (FSH) and leutinizing hormone (LH)), erythropoietin (EPO), GM-CSF, G-CSF, IL-10, growth regulatory factor (GRF) and glucagons.

In all cases, after a coating has been applied, the coating solution is dried onto the microprotrusions by various means. In a preferred embodiment the coated device is dried in ambient room conditions. However, various temperatures and humidity levels can be used to dry the coating solution onto the microprotrusions. Additionally, the devices can be heated, lyophilized, freeze dried or similar techniques used to remove the water from the coating.

Other known formulation adjuvants can be added to the coating solution as long as they do not adversely affect the necessary solubility and viscosity characteristics of the coating solution and the physical integrity of the dried coating.

The following examples are given to enable those skilled in the art to more clearly understand and practice the present invention. They should not be considered as limiting the scope of the invention but merely as being illustrated as representative thereof.

Example 1

A coated microprotrusion device for transdermally delivering desmopressin was prepared in the following manner. An aqueous desmopressin solution having a concentration of 300 mg/ml was prepared by adding desmopressin monoacetate salt (sold by Diosynth, Inc. of Des Plaines, Ill.) to sterile distilled water. Tritium labeled desmopressin was added to the desmopressin solution as a marker. A titanium microprotrusion member of the type illustrated in FIG. 1 was used. The microprotrusion member had a circular shape (1.16 cm diameter sheet with an area of 2 $cm^2$), microprotrusions with a length of 360 µm, and a microprotrusion density of 190 microprotrusions/$cm^2$. The microprotrusion member was immersed briefly in the aqueous desmopressin solution and allowed to dry overnight at room temperature. This procedure resulted in a desmopressin coated microprotrusion member having a coating containing desmopressin in the amount of 150 to 250 µg/$cm^2$ of the sheet.

Figure 3:
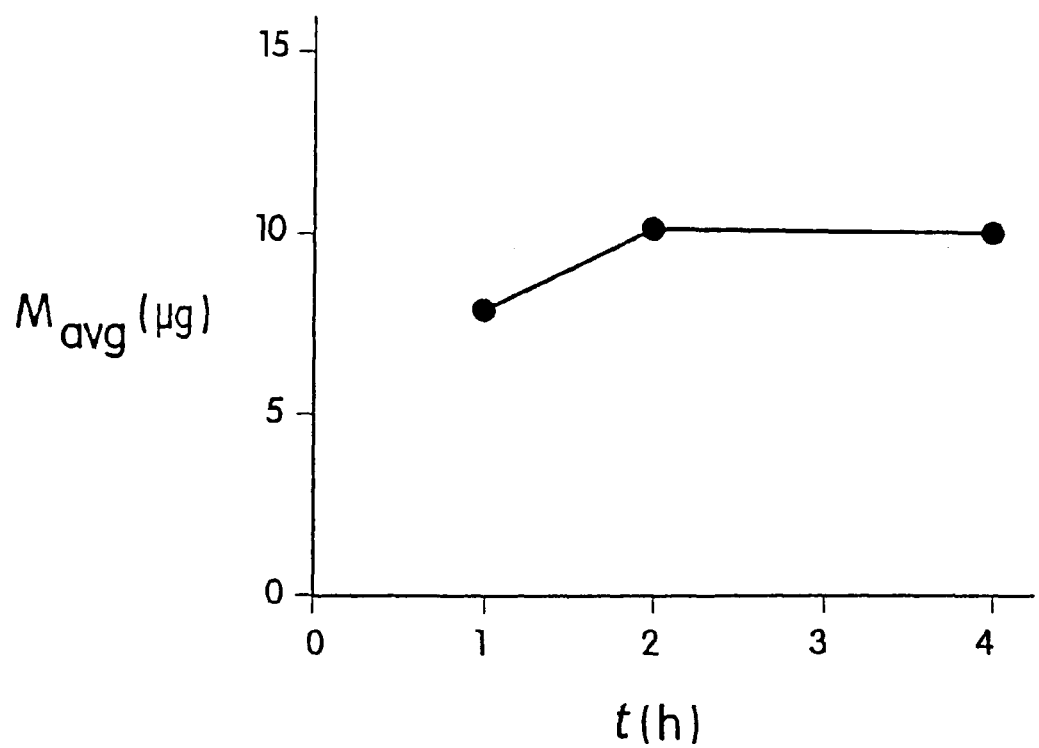
FIG. 3 is a graph showing the amount of desmopressin delivered by a microprotrusion array.
Figure 7:
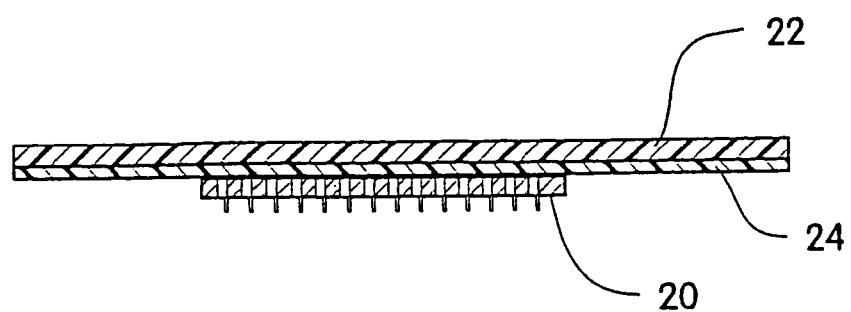
FIG. 7 is a side sectional view of the system described in Example 1.
Figure 8:
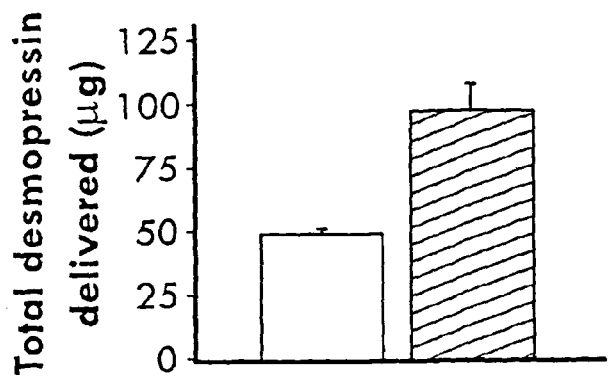
FIG. 8. is a graph showing the amount of desmopressin delivered by a microprotrusion array that has been tip-coated as described in Example 2B.
Figure 9:
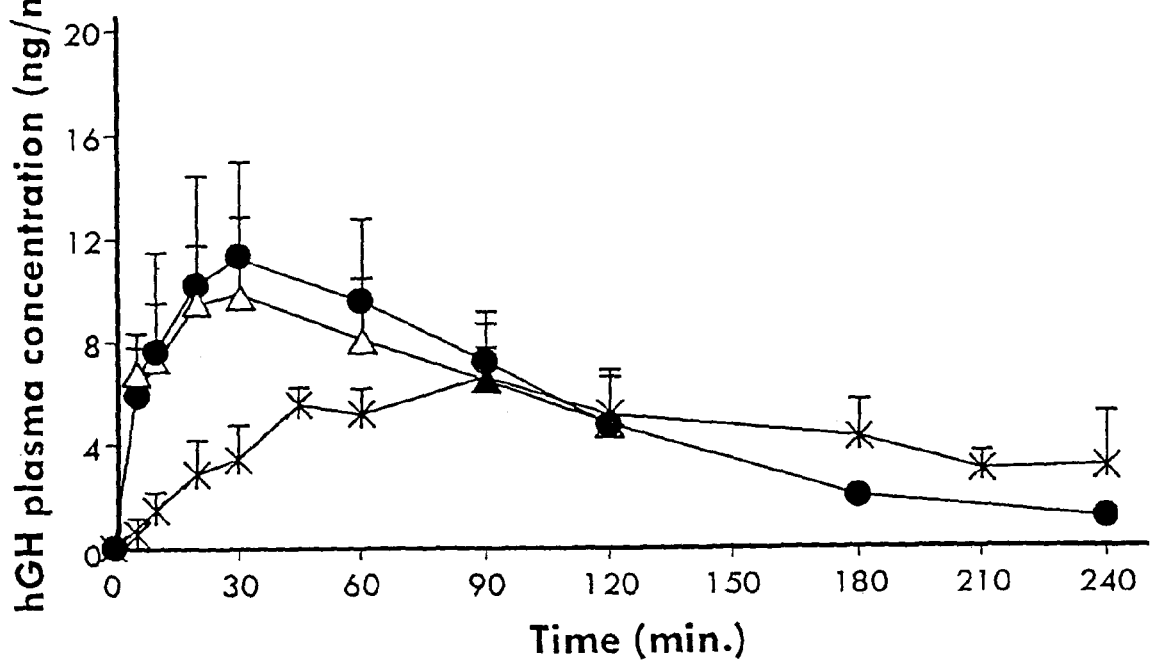
FIG. 9 is a graph showing the amount of human growth hormone delivery by a microprotrusion array that has been tip-coated as described in Example 4B.

Delivery kinetics studies were performed in twelve hairless guinea pigs (HGPs) to evaluate the kinetics of drug absorption through the skin from the coated microprotrusion members prepared as described above. The system applied is shown in FIG. 7. System 25 was comprised of the coated circular microprotrusion member 20 adhered to the middle portion of a low density polyethylene (LDPE) sheet 22 having an adhesive film 24 on the skin proximal side of the LDPE sheet 22 between sheet 22 and microprotrusion member 20. The LDPE sheet 22 and the adhesive film 24 act as an adhesive overlay which keeps the microprotrusion member adhered to the animal's skin. The skin of one HGP flank was manually stretched bilaterally (√ and •) at the time of applying the microprotrusion member to the animal. The system was impacted against the animals' skin using a spring-loaded impact applicator which caused the microprotrusions to pierce the stratum corneum. Following application of the system, the stretching tension on the skin was released, the HGP was wrapped with a Vetwrap™ bandage and housed individually in a metabolic cage for 1, 2 or 4 hours. At each time point, four of the HGPs had their systems removed and residual drug was thoroughly washed from the skin and the animal was returned to its cage. The total amount of drug delivered systemically during these time intervals was determined by measuring the radioactivity of excreted urine for two days following system removal and corrected from the percentage excreted following IV injection (previous studies had shown that 60% of the injected dose of $^3$H-desmopressin was excreted in urine over 48 hours). The average amount of desmopressin delivered to the HGPs ($M_{avg}$) during hours 1, 2 and 4 of wear is presented in FIG. 3. After the first two hours, no additional amount of drug was absorbed. Total amount of desmopressin delivered was about 10 micrograms, which is known to be a therapeutically effective dose in humans for treatment of nocturnal enuresis.

Example 2A

Figure 4:
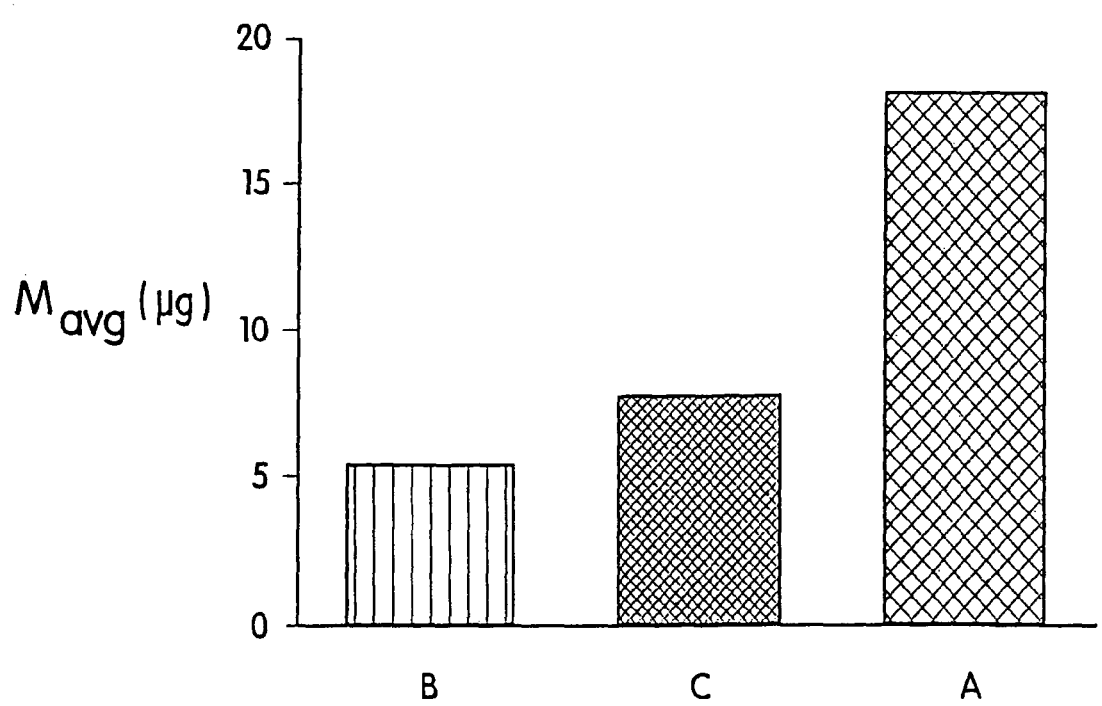
FIG. 4 is a graph showing the amount of desmopressin delivered by a microprotrusion array.

A second experiment was performed on hairless guinea pigs (HGPs). All animals wore a system identical to those previously described in Example 1. One group of animals (Group A) wore a system for 1 hour. In two other groups (Groups B and C), the microprotrusion device was removed 5 seconds after application. In Group B, the treatment site was immediately washed after removal of the system. In Group C, the treatment site was not washed but was occluded with an adhesive backing for 1 hour following system removal. The average amounts of desmopressin delivered to the animals in Groups A, B and C are shown in FIG. 4. Group B (5 second delivery and immediate washing) resulted in an average delivery of about 5 µg desmopressin. Group C (occlusion following 5 second application) did not increase significantly the amount delivered to Group B. Group A (one hour delivery) resulted in an average of 18 µg desmopressin delivered. These results indicate that keeping the coated microprotrusions in piercing relation to the skin for only about 5 seconds results in substantial, although not optimal, delivery of desmopressin and that the drug delivered into the skin is not removed by washing. In addition, prolonged (1 hour) contact of the microprotrusions with the skin results in even greater amounts of desmopressin delivered.

Example 2B

The feasibility of coating a microprotrusion array with the drug desmopressin was evaluated. In these studies the coating was limited to the tips of the microprotrusions. A number of microprotrusion arrays (S250 Ti, microprotrusion length 250 µm, 321 microprotrusions/$cm^2$, 2 $cm^2$ disc) were tip coated using the device described in a U.S. provisional patent (Ser. No. 60/276,762, filed 16 Mar. 2001) using a 40 wt % desmopressin acetate solution spiked with $^3$H desmopressin. Analysis revealed that each microprotrusion array was coated with 187±30 µg desmopressin. SEM examination revealed that the coating was present as a glassy amorphous matrix with good uniformity of coating from microprotrusion to microprotrusion. The coating was limited to the first 115 µm of the 250 µm microprotrusion. The coating was found unevenly distributed on the microprotrusion itself. Most of the solid coating appeared to be located in circular domed regions of the coating called a cap, centered on the geometric center of the faces of the coated area of the microprotrusion. The maximum measured thickness of the coating was about 18 µm while the average calculated thickness over the entire coated area was only about 13 µm.

Figure 5:
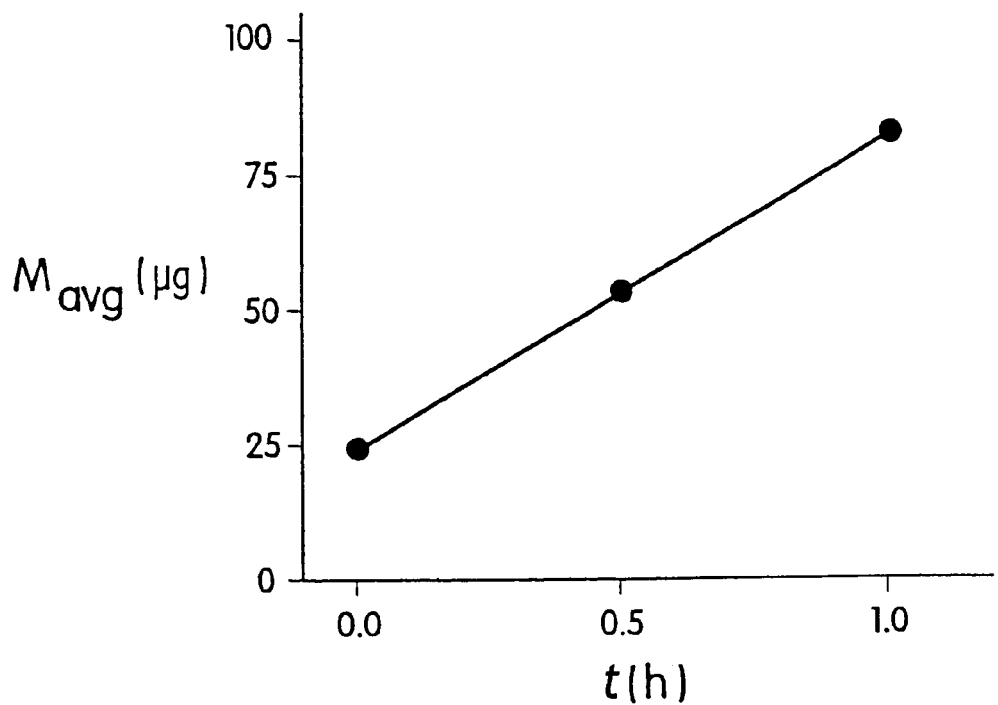
FIG. 5 is a graph showing the amount of ovalbumin delivered by a microprotrusion array for various application times.

Studies were performed in hairless guinea pigs to evaluate the kinetics of drug absorption through the skin from desmopressin tip-coated microprotrusion array systems. System application was performed on the flank of the animal with an impact applicator delivering an energy of 0.26 J in less than 10 ms. The system applied comprised a coated microprotrusion array device, adhered to the center of a LDPE backing with adhesive (7 $cm^2$ disc). Systems remained on the skin for 5 seconds or 1 hour. Groups of three animals were used for both time points. Upon removal of the system, the application site was thoroughly cleaned and the washes were evaluated for radioactive content and the HGPs were returned to their individual metabolism cages. Urine was collected for 2 days and counted for radioactive content. The total amount of drug delivered systemically was determined by measuring urinary excretion of radioactivity for two days following system removal and corrected from the percentage excreted following iv injection (previous studies had shown that 60% of the injected dose of $^3$H-desmopressin was excreted in urine over 48 hours). The used systems were extracted for residual radioactivity. Total amounts of desmopressin delivered systemically were 49±3 μg (26% drug utilization) and 97±11 μg (52% drug utilization) following 5 seconds (open bar) and 1 hour (hatched bar) wearing times, respectively (FIG. 8). Only a small percentage of the drug was found on the surface of the skin (6% at 5 seconds, and 9% at 1 hour), the balance consisting of desmopressin remaining on the microprotrusions.

Example 3

The properties of the desmopressin coating were evaluated in the following manner. Fluorescein sodium salt was added to a 300 mg/ml solution of desmopressin in water. Sufficient fluorescein sodium salt was added to achieve a final concentration of 0.001M.

A titanium foil (0.025 mm thick) was immersed briefly in this solution and allowed to dry overnight at room temperature. Fluorescence microscopy revealed that the dry film of desmopressin was amorphous in nature and behaved much like a transparent glass. A coating of about 2 μm thick appeared to behave best in terms of flexibility and adherence to the titanium sheet. Coatings thicker than about 10 μm were found to be brittle and susceptible to cracking.

Example 4A

Human growth hormone (hGH) was added to sterile distilled water to form an aqueous hGH solution having an hGH concentration of about 200 mg/ml and a viscosity of less than 50 cp. A titanium foil was immersed in the solution, followed by drying overnight at room temperature to form the hGH coating. Adequate coating of the foil was demonstrated by microscopy utilizing the method previously discussed. Although hGH could not be used for therapeutic purposes with this strategy because of the large therapeutic dose it requires, it is believed to be a good model for cytokines, particularly interferons, which require a much smaller therapeutic dose. Similarly, titanium foil was coated with an aqueous solution of ovalbumin, a 45,000 Dalton polypeptide containing an oligosaccharide side chain. The solution had an ovalbumin concentration of about 300 mg/ml and a viscosity of less than 50 centipoises. Adequate coating of the titanium foil was demonstrated by microscopy utilizing the method previously discussed. Although ovalbumin is not a pharmacologically active agent used in therapeutics or as defined herein, it is a good model for large pharmacological agents such as follicle stimulating hormone (FSH) and erythropoietin.

Example 4B

The feasibility of coating a microprotrusion array with the drug hGH was evaluated. In these studies the coating was limited to the tips of the microprotrusions. Microprotrusion arrays (S250 Ti, microprotrusion length 250 μm, 321 microprotrusions/$cm^2$, 2 $cm^2$ disc) were tip coated using the device described in a U.S. provisional patent application (Ser. No. 60/276,762, filed 16 Mar. 2001) using a 20 wt % hGH, 20 wt % sucrose coating solution. Analysis revealed that each microprotrusion array was coated with 9.5±0.9 μg hGH. SEM revealed good uniformity of coating from microprotrusion to microprotrusion with a coating depth of about 100 μm. However, on the microprotrusion itself, the coating was found unevenly distributed. Most of the solid coating appeared to be located in caps centered on the geometric center of the faces of the coated area of the microprotrusion. Following two days storage in a vacuum chamber the solid coating presented a very smooth surface with absence of cracking and it was demonstrated to adhere very tightly to the microprotrusions. The maximum measured thickness of the coating was about 4 μm while the average calculated thickness over the entire coated area was only about 1.7 μm.

Studies were performed in hairless guinea pigs to evaluate the kinetics of drug absorption through the skin from hGH tip-coated microprotrusion array systems. System application was performed on the flank of the anesthetized animals with an impact applicator delivering an energy of 0.26 J in less than 10 milliseconds. The system applied comprised a coated microprotrusion array device, adhered to the center of a LDPE backing with an adhesive (7 $cm^2$ disc). Systems remained on the skin for 5 seconds (n=3) or 5 minutes (n=5). A group of animals (n=5) received a subcutaneous injection of 10 μg hGH. Blood samples were collected at time intervals for plasma hGH determination by ELISA. The hGH dose delivered was extrapolated based on an area under the curve (AUC) calculation compared to IV administration of hGH. Results showed that hGH delivery from the microprotrusion array was the same with 5 seconds (open triangles) and 5 minutes (close circle) wearing times (FIG. 9). On average, 5 μg of hGH was delivered in each animal, which accounts for approximately 50% of the coated dose. This is to compare with a bioavailability of 65% following subcutaneous administration of hGH, the results of which are shown as "X" (FIG. 9).

Example 5

The feasibility of coating the microprotrusion devices with ovalbumin was evaluated. A coating solution comprising 200 mg/ml of fluorescein-tagged ovalbumin in water was prepared. The microprotrusion member of the type used in Example 1 was immersed briefly in the coating solution, blown dry, and allowed to dry overnight at room temperature. Subsequent analysis demonstrated that this coating procedure resulted in microprotrusions coated with ovalbumin at 200 to 250 μg per $cm^2$ of the microprotrusion member.

Studies were performed in hairless guinea pigs (HGPs) to evaluate the kinetics of ovalbumin absorption into the skin from coated microprotrusions devices. The applied system comprised a coated microprotrusion device, adhered to the center of a LDPE backing with an adhesive housed on a 3.8 cm² disc. The skin of one HGP flank was manually stretched bilaterally (√ and •) at the time of the application of the system. Microprotrusion application was performed using a spring loaded applicator which impacted the system against the animal's skin. Following application, the stretching tension was released, the HGPs were wrapped with a Vetwrap™ bandage and housed individually in a metabolic cage for 30 minutes or 1 hour. At each time point, four HGPs had their systems removed and residual drug was thoroughly washed from the skin and the animal was returned to its cage. In one group of HGPs, the microprotrusion device was removed 5 seconds after application (0 hour time point). The average total amount of ovalbumin delivered into the skin ($M_{avg}$) during these time intervals was determined by taking an 8 mm skin biopsy at the application site. The skin biopsy sample was then dissolved in hyamine hydroxide (diisobutylcresoxyethoxyethyl) dimethyl) benzylammonium hydroxide, 1 M in ethanol, sold by J. T. Baker (NJ, USA) and the amount of ovalbumin present was determined by fluorimetry. Results demonstrated that up to 80 µg ovalbumin was delivered intracutaneously over the 1 hour application period. The 5 second piercing resulted in about 25 µg of ovalbumin delivered intracutaneously. These results are shown in FIG. 5. Although ovalbumin is not a pharmacological agent used in therapeutics, it is a good model for large potent pharmacologically active agents such as follicle stimulating hormone and erythropoietin.

Example 6A

Figure 6:
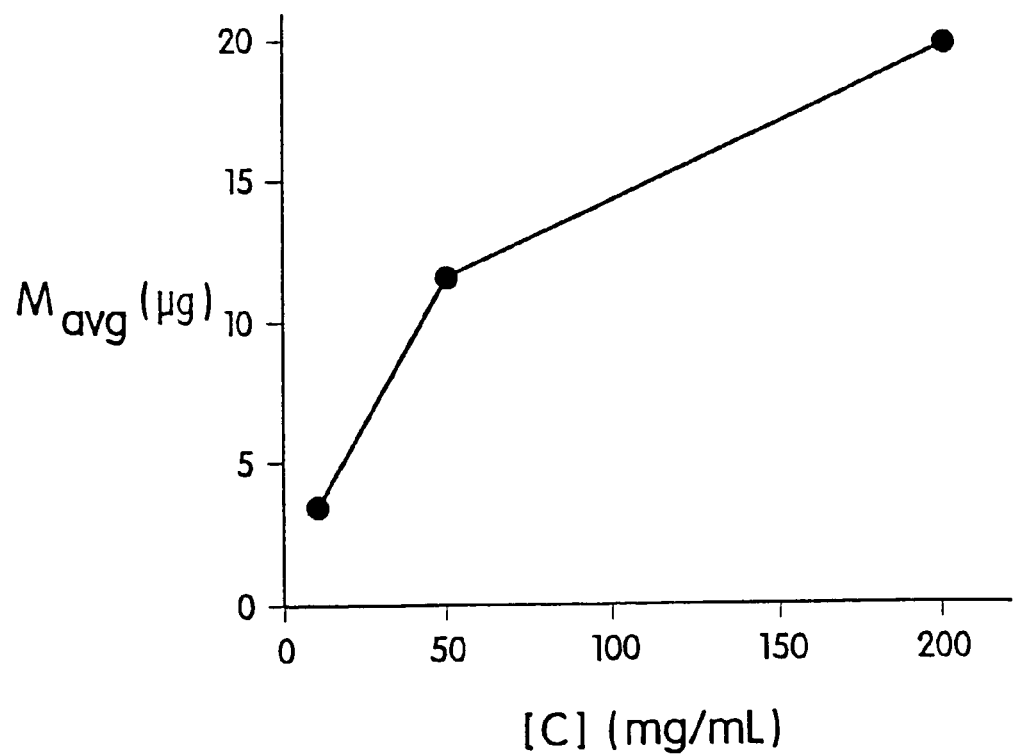
FIG. 6 is a graph showing the amount of ovalbumin delivered by a microprotrusion array using various coating solutions of ovalbumin.

An experiment similar to that described in Example 1 was performed in the HGPs using the identical microprotrusion systems which were coated with aqueous ovalbumin solutions having ovalbumin concentrations of 200, 50, and 10 mg/ml ovalbumin. In all groups the microprotrusion device was removed immediately after application. Application and analysis were performed identically to that described in Example 1. Results demonstrated that delivery of ovalbumin could be controlled by controlling the amounts coated on the microprotrusions. The average amounts of ovalbumin delivered ($M_{avg}$) for each of the three solution concentrations ([C]) are shown in FIG. 6.

Example 6B

The feasibility of coating a microprotrusion array with the drug ovalbumin was evaluated. In these studies the coating was limited to the tips of the microprotrusions. Microprotrusion arrays (S250 Ti, microprojection length 250 µm, 321 microprojections/cm², 2 cm² disc) were tip coated using the device described in a U.S. provisional patent application (Ser. No. 60/276,762; filed 16 Mar. 2001) using a 20 wt % ovalbumin tagged with fluorescein isothiocyanate (FITC). Analysis revealed that each microprotrusion array was coated with 4.6±0.5 µg ovalbumin. SEM examination revealed that the coating was present as a glassy amorphous matrix with good uniformity of coating from microprojection to microprojection. The coating was limited to the first 150 µm of the microprojection.

Figure 10:
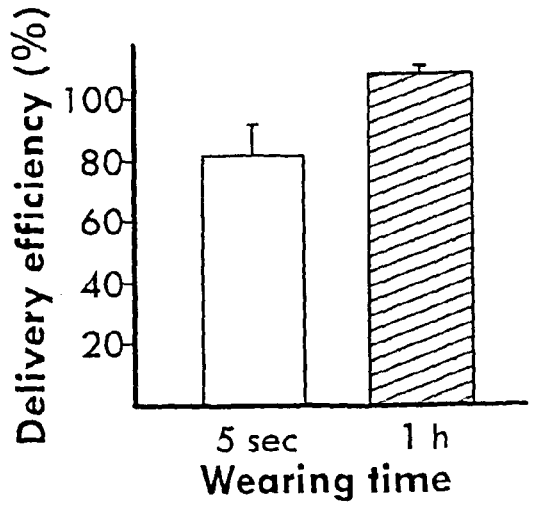
FIG. 10 is a graph showing the delivery efficiency of ovalbumin aministered by a microprotrusion array that has been tip-coated as described in Example 6B.

Studies were performed in euthanized hairless guinea pigs to evaluate the kinetics of drug absorption through the skin from ovalbumin tip-coated microprotrusion array systems. System application was performed on the flank of the animal with an impact applicator delivering an energy of 0.26 J in less than 10 ms. The applied systems comprised a coated microprotrusion array, adhered to the center of a LDPE backing with an adhesive (7 cm² disc). Systems remained on the skin for 5 seconds or 1 hour. Groups of three animals were used for both time points. At the end of the wearing time, the system was removed and the skin wiped clean of any residual drug. The total amount of ovalbumin delivered in the skin during these time intervals was determined by dissolving a 8 mm skin biopsy in hyamine hydroxide (10% in methanol). Quantitation was performed by fluorimetry. Results presented in FIG. 10 demonstrated that more than 80% of the ovalbumin dose was delivered after 5 seconds wearing time (open bar). Close to 100% of the dose had been delivered after 1 hour application time (solid bar).

Although the present invention has been described with reference to specific examples, it should be understood that various modifications and variations can be easily made by a person having ordinary skill in the art without departing from the spirit and scope of the invention. Accordingly, the foregoing disclosure should be interpreted as illustrative only and not to be interpreted in a limiting sense. The present invention is limited only by the scope of the following claims.

What is claimed is:

1. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um, and a dry coating on said member; said coating, before drying, comprising an aqueous solution of an amount of a pharmacologically active agent; wherein said pharmacologically active agent is sufficiently potent to be therapeutically effective when administered without the use of electricity in an amount less than 1 milligram, said agent having aqueous solubility at 25° C. of greater than 50 mg/ml and said aqueous solution having a viscosity at 25° C. of less than 500 centipoises, wherein said device further comprises a spring-loaded impact applicator.

2. A passive transdermal drug delivery system comprising a device for transdermally delivering a pharmacologically active agent via passive diffusion, the device comprising: a member having a plurality of stratum corneum-piercing microprotrusions and a dry coating only on one or more of said microprotrusions, wherein said microprotrusions have a width and thickness ranging from 5 to 50 um; said coating, before drying, comprising an aqueous solution of an amount of a pharmacologically active agent; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

3. A passive transdermal drug delivery system comprising a device for transdermally delivering a pharmacologically active agent via passive diffusion, the device comprising: a member having a plurality of stratum corneum-piercing microprotrusions, said microprotrusions being adapted to pierce through the stratum corneum to a depth of less than 500 micrometers, said microprotrusions having a width and thickness ranging from 5 to 50 um; and a dry coating on said member; said coating, before drying, comprising an aqueous solution of an amount of a pharmacologically active agent; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

4. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent; said coating having a thickness equal to or less than the thickness of the microprotrusions; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

5. A passive transdermal drug delivery system comprising a device for transdermally delivering a pharmacologically active agent via passive diffusion, the device comprising: a member having a plurality of stratum corneum-piercing microprotrusions, said microprotrusions having a length of less than 500 micrometers and a thickness of less than 25 micrometers; and a dry coating on said member; said coating, before drying, comprising an aqueous solution of an amount of a pharmacologically active agent; wherein said pharmacologically active agent is sufficiently potent to be therapeutically effective when administered without the use of electricity in an amount less than 1 mg, said agent having aqueous solubility at 25° C. of less than 500 centipoises, wherein said device further comprises a spring-loaded impact applicator.

6. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um, said microprotrusions having been formed by etching said plurality of microprotrusions from a thin sheet and folding the microprotrusions out of a plane of the sheet; and a dry coating on said member; said coating, before drying, comprising an aqueous solution of an amount of a pharmacologically active agent; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

7. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent; said pharmacologically active agent being sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises; and wherein the pharmacologically active agent is selected from the group consisting of adrenocortiocotropic hormone (ACTH (1-24)), calcitonin, desmopressin, leutinizing hormone releasing hormone (LHRH), goserelin, leuprolide, buserelin, triptorelin, other LHRH analogs, parathyroid hormone (PTH), vasopressin, deamino [Val4, D-Arg8] arginine vasopressin, interferon alpha, interferon beta, interferon gamma, follicle stimulating hormone (FSH), erythropoietin (EPO), granulocyte macrophage colony stimulating factor (GM-CSF), granulocyte colony stimulating factor (G-CSF), interleukin-10 (IL-10), glucagon, growth regulatory factor (GRF), analogs thereof and pharmaceutically acceptable salts thereof, wherein said device further comprises a spring-loaded impact applicator.

8. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of the pharmacologically active agent desmopressin; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

9. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent, said coating having been applied by dip coating; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

10. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent, said coating having been applied by spray coating; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

11. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent, said coating having been applied by spray coating; said spray comprising droplets having a volume of 10 picoliters to about 200 picoliters; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

12. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry non-contiguous coating on said member; said coating, before drying, comprising an aqueous solution of an amount of a pharmacologically active agent; wherein said pharmacologically active agent is sufficiently potent to be therapeutically effective when administered without the use of electricity in an amount less than 1 mg, said agent having aqueous solubility at 25° C. of greater than 50 mg/ml and said aqueous solution having a viscosity at 25° C. of less than 500 centipoises, wherein said device further comprises a spring-loaded impact applicator.

13. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent; wherein said pharmacologically active agent is sufficiently potent to be therapeutically effective when administered without the use of electricity in an amount less than 0.25 milligrams, said agent having aqueous solubility at 25° C. of greater than 50 mg/ml and said aqueous solution having a viscosity at 25° C. of less than 500 centipoises, wherein said device further comprises a spring-loaded impact applicator.

14. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent; wherein said pharmacologically active agent is sufficiently potent to be therapeutically effective when administered without the use of electricity in an amount less than 1 mg, said agent having aqueous solubility at 25° C. of greater than 50 mg/ml and said aqueous solution having a viscosity at 25° C. of less than 50 centipoises, wherein said device further comprises a spring-loaded impact applicator.

15. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent, said coating having a thickness over a surface of said member of less than 50 micrometers; wherein said pharmacologically active agent is sufficiently potent to be therapeutically effective when administered without the use of electricity in an amount less than 1 mg, said agent having aqueous solubility at 25° C. of greater than 50 mg/ml and said aqueous solution having a viscosity at 25° C. of less than 500 centipoises, wherein said device further comprises a spring-loaded impact applicator.

16. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent, said coating having a thickness over a surface of said member of less than 25 micrometers; wherein said pharmacologically active agent is sufficiently potent to be therapeutically effective when administered without the use of electricity in an amount less than 1 mg, said agent having aqueous solubility at 25° C. of greater than 50 milligrams/milliliter and said aqueous solution having a viscosity at 25° C. of less than 500 centipoises, wherein said device further comprises a spring-loaded impact applicator.

17. A passive transdermal drug delivery system comprising a device for transdermally delivering a pharmacologically active agent via passive diffusion, the device comprising: a member having a plurality of stratum corneum-piercing microprotrusions, said microprotrusions having a width and thickness ranging from 5 to 50 um; and a dry coating on said member; said coating, before drying, comprising an aqueous solution of an amount of a pharmacologically active agent and an adjuvant; wherein said pharmacologically active agent is sufficiently potent to be therapeutically effective when administered without the use of electricity in an amount less than 1 mg, said agent having aqueous solubility at 25° C. of greater than 50 mg/mL and said aqueous solution having a viscosity at 25° C. of less than 500 centipoise, wherein said device further comprises a spring-loaded impact applicator.

* * * * *